United States Patent [19]

Andrews et al.

[11] Patent Number: 4,559,671
[45] Date of Patent: Dec. 24, 1985

[54] STERILE HANDLE COVER FOR SURGICAL LAMP

[75] Inventors: Winston A. Andrews, Clearwater; Larry Carpenter, St. Petersburg, both of Fla.

[73] Assignee: Medical Research Associates Ltd. #2, Clearwater, Fla.

[21] Appl. No.: 606,237

[22] Filed: May 2, 1984

[51] Int. Cl.⁴ .............................................. B25G 1/02
[52] U.S. Cl. ............................ 16/111 R; 16/114 R; 16/DIG. 19; 16/DIG. 24; 362/804
[58] Field of Search ............ 16/110 R, 110 A, 111 R, 16/114 R, 114 A, DIG. 12, DIG. 18, DIG. 19, DIG. 24; 74/551.9, 557; 362/804

[56] References Cited

U.S. PATENT DOCUMENTS

| | | | |
|---|---|---|---|
| 2,815,679 | 12/1957 | Roberts | 74/551.9 |
| 3,251,241 | 5/1966 | Francis | 74/551.9 |
| 4,316,237 | 2/1982 | Yamada et al. | 362/804 X |
| 4,386,179 | 5/1983 | Sterling | 524/269 |

FOREIGN PATENT DOCUMENTS 73780 1/1952 Denmark ........................ 74/551.9

Primary Examiner—Fred Silverberg
Attorney, Agent, or Firm—Frijouf, Rust & Pyle

[57] ABSTRACT

A sterile handle cover is disclosed for covering a lamp handle of a surgical lamp to provide a sterile surface for adjustment of the lamp by an operator. The handle cover comprises a grip portion defined by a first and a second end. An end wall is integrally attached proximate the first end of the grip portion to form a hollow container open at the second end. A protector is connected to the second end of the grip portion and extends radially outwardly for protecting the hand of the operator from contacting portions of the surgical lamp proximate the lamp handle. A plurality of ribs are disposed in the grip portion for frictionally engaging the lamp handle of the surgical lamp to maintain the position of the handle cover thereon.

6 Claims, 11 Drawing Figures

STERILE HANDLE COVER FOR SURGICAL LAMP

BACKGROUND OF THE INVENTION

1. Field of the Invention

The invention relates to medical apparati and, more particularly, to a sterile handle cover for a surgical lamp.

2. Background of the Invention

The rising cost of medical care and medical treatment has challenged administrators of medical facilities and has encouraged such administrators to look for techniques and devices to reduce the operating costs of the medical facility. Various types of devices and techniques have been proposed by the prior art in an effort to reduce the ever-increasing cost of medical care.

One area of concern where cost reduction has been sought resides in the sterilization of medical equipment. All medical devices and instruments used in proximity to patients have to be sterilized by the medical facility prior to use. This sterilization is typically accomplished by sterilizers installed within the medical facility which are designed for accommodating devices and instruments which are immediately required by the medical facility. With the ever-increasing number and design of medical instruments, the problems associated with sterilizing a large number of instruments of various sizes and shapes creates a substantial burden on the medical facility. In particular, in operating rooms, where incisions are made into the patient, all surfaces which may come in contact with the surgeon must be sterile prior to the commencement of the operation. The sterilization of all surfaces in which the surgeon may come in contact has become extemely burdensome for the medical facility, in view of the increasing number of devices, machines and apparati now present in the typical operating room.

Accordingly, medical facilities have looked toward disposable sterile covers for the various surfaces of the operating room which will be contacted by the operating surgeon. These disposable sterile covers are generally cost effective, since the covers may be mass produced and mass sterilized by a medical manufacturer in contrast to the sterilization normally affected within a medical facility. Furthermore, the disposable, pre-sterilized covers have the advantage of being readily available for emergency operations which are not planned by the medical facility. Accordingly, the use of disposable sterile covers within the medical facility has proved to be cost effective in the relatively recent history thereof.

In an operating room, the patient is typically placed on a table under an operating room lamp for illuminating the point of incision for the surgeon. During the course of the operation, the direction of illumination of the operating room lamp is generally changed, depending upon the position of the patient and the personnel in attendance at the operation. Many physicians desire to adjust the operating room lamp personally, rather than verbally direct another in the adjustment so that the exact point to be illuminated may be obtained by the physician. Accordingly, the light handle of a surgical lamp or an operating room lamp almost certainly will come in contact with the hand of the surgeon, and accordingly, the light handle of an operating room lamp must either be protected by a sterile handle cover or must be sterilized by conventional means.

Many among the prior art have attempted to provide sterile light handle covers for surgical lamps, utilizing a generally-cylindrical handle portion with a conical protector extending from one end thereof. These devices were typically made of a unitary piece of flexible plastic or rubber material for insertion on the generally-cylindrical handle of the surgical lamp. Although these devices have provided an important improvement in the medical art, the devices had several disadvantages. First, the devices, when applied to the light handle cover, were difficult to remove after the operation was completed due to suction created by the generally cylindrical handle portion. Second, the covers were of limited size and, accordingly, did not provide adequate protection from the hand of the surgeon when touching surfaces adjacent to the lamp handle when the surgeon was attentive on the incision area and not actively looking at the lamp handle. Accordingly, if the surgeon inadvertantly touched a non-sterile area of the surgical lamp, the surgeon must retire and resterilize before returning to the operation. Such a resterilization results in an enormous increase in medical costs, as well as an unnecessary use of an operating room facility.

It is the primary object of the present invention to provide a sterile handle cover that overcomes the inadequacies of the prior art devices and provides an improvement which significantly contributes to the maintenance of a sterile condition in an operating room.

Another object of this invention is to provide a sterile handle cover for covering the lamp handle of a surgical lamp, which incorporates a grip portion defined by a first and a second end, with an end wall integrally attached to the first end and with a cone-shaped protector connected to the second end and extending radially outward therefrom, with a plurality of ribs disposed in the grip portion for frictionally engaging the lamp handle of the surgical lamp.

Another object of this invention is to provide a sterile handle cover for covering the lamp handle of a surgical lamp, wherein the ribs extend longitudinally along the length of the grip portion, and at least one of the grip portion and the plurality of ribs is tapered for effecting the frictional engagement with the lamp handle and providing easy removal of the handle cover subsequent to the medical treatment.

Another object of this invention is to provide a sterile handle cover for covering the lamp handle of a surgical lamp, incorporating a second cone-shaped protector which is connected to the outer periphery of the cone-shaped protector, enabling the second cone-shaped protector to be disposed in a first and a second bistable position to either increase the area of protection provided by the handle protector or to function as a locating device for the hand of the physician.

Another object of this invention is to provide a sterile handle cover for covering the lamp handle of a surgical lamp, which may be readily produced as a unitary member of a flexible plastic or rubber material.

Another object of this invention is to provide a sterile handle cover for covering the lamp handle of a surgical lamp, which is readily adapted to be a pre-sterilized and packaged as a disposable product.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention within the scope of the invention. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention may be incorporated into an apparatus and a method relating to a sterile handle cover for covering a lamp handle of a surgical lamp to provide a sterile surface for adjustment of the lamp by an operator. The sterile handle cover comprises a grip portion defined by a first and a second end. An end wall is integrally attached proximate the first end of the grip portion to form a hollow container open at the second end. A protector means is connected to the second end of the grip portion and extends radially outwardly for protecting the hand of the operator from contacting portions of the surgical lamp proximate the lamp handle. A plurality of ribs are disposed in the grip portion for frictionally engaging the lamp handle to maintain the position of the handle cover theron.

In a more specific embodiment of the invention, the plurality of ribs are integrally molded into an interior surface of the grip portion. The grip portion may be tapered between the first and second ends or, alternatively, the plurality of ribs may extend longitudinally along the length of the grip portion with each of the plurality of ribs being tapered along the length thereof. In still another embodiment, the grip portion is tapered between the first and second ends, and the plurality of ribs are also tapered to complement the taper of the grip portion for providing frictional engagement with the lamp handle of the surgical lamp.

Preferably, the protector means is cone shaped and is connected to the second end of the grip portion by an integral connector means having a reduced wall thickness. A plurality of cone ribs may extend radially about the cone-shaped protector for increasing the mechanical strength thereof. Preferably, the plurality of cone ribs are uniformly spaced about the cone-shaped protector.

The invention may also include a second cone-shaped protector integrally connected to the outer periphery of a first cone-shaped protector by an integral reduced wall second connector means. The second connector means enables the second cone-shaped protector to be disposed in one of a first and a second bistable position. The second cone-shaped protector extends generally in the same direction as the first cone protector in the first bistable position for increasing the area of protection from the hand of the operator. The second cone protector may optionally extend at an angle relative to the cone portion in the second bistable position to function as a sterile locating portion for the hand of the operator.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the present invention, reference should be hand to the following detailed description taken in connection with the accompanying drawings in which.

Similar reference characters refer to similar parts through the several views of the drawings.

DETAILED DESCRIPTION

Figure 1:
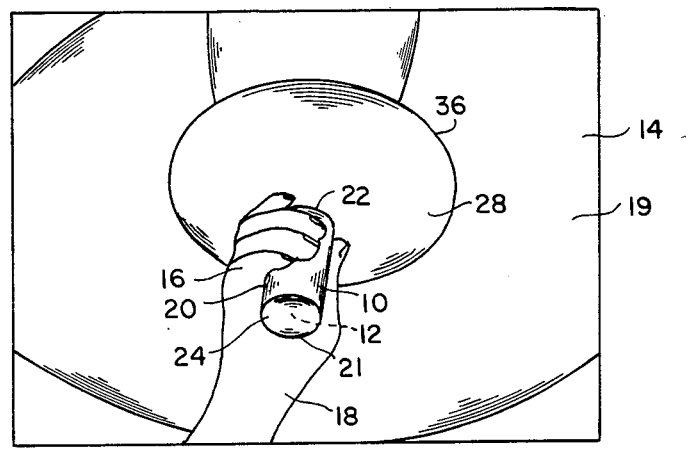
FIG. 1 is a perspective view of the handle cover of the present invention when applied to a surgical lamp.

FIG. 1 is a perspective view of an improved sterile handle cover 10 for covering a lamp handle 12 of a surgical lamp 14 to provide a sterile surface for contact by a hand 16 of an operator 18. The surgical lamp 14 is shown as an operating room lamp having a lamp reflector 19 and is typically mounted on pivot means (not shown) for adjusting the position of the beam of the lamp relative to a patient. The adjustment of the position of the beam of the lamp is affected by the operator 18 moving the handle 12 of the surgical lamp 14 to an appropriate position. Many physicians and/or surgical personnel prefer to personally adjust the position of the beam of the surgical lamp 14, rather than verbally directing another person adjusting the lamp, thereby obtaining the exact position desired and effective the adjustment in a quicker period of time. Although the present invention has been shown in FIG. 1 as being applied to an operating room surgical lamp, it should be understood that the invention as hereinafter described and claimed is suitable for use with other types of surgical lamps and the like in the offices of physicians, emergency rooms and dental offices.

Figure 2:
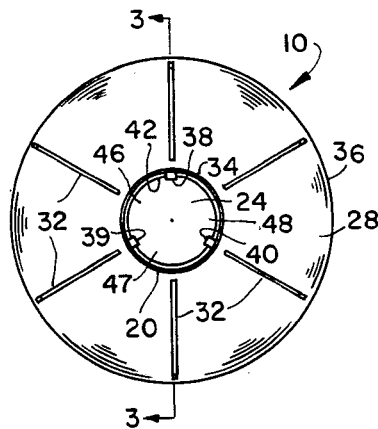
FIG. 2 is a top view of the handle cover shown in FIG. 1.
Figure 3:
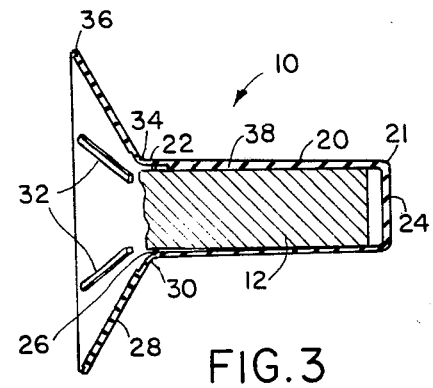
FIG. 3 is a sectional view along line 3—3 of FIG. 2.
Figure 4:
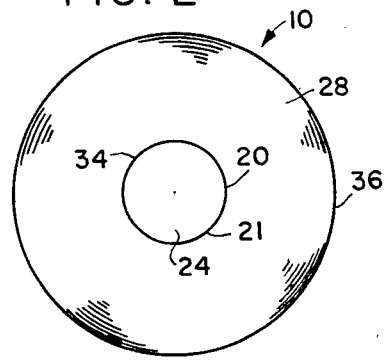
FIG. 4 is a bottom view of the handle cover shown in FIG. 1.

The sterile handle cover 10 comprises a grip portion 20 having a first end 21 and a second end 22. The grip portion 20 is preferably made of a resilient material such as plastic or rubber, and having an end wall 24 extending across the first end 21, creating a hollow opening 26 for completely encompassing the handle 12 of the lamp 14 as shown in FIG. 3. A protector means 28 shown as being substantially cone shaped is connected to the second end 22 of the grip portion 20 and extends radially outwardly for protecting the hand 16 of the operator 18 from contacting portions of the surgical lamp 14 proximate the lamp handle 12. The protector means 28 is connected to the second end 22 by a first connector means 30, comprising an integral reduced-wall thickness region for allowing flexibility of the cone-shaped protector means 28 relative to the grip portion 20. The cone-shaped protector means 28, as best shown in FIG. 2, includes a plurality of radially-extending protector ribs 32 to add mechanical strength to the cone-shaped protector means 28. The plurality of protector ribs 32 terminate short of a proximal edge 34 and a distal edge 36 of the cone-shaped protector means 28. Although six protector ribs have been shown in this embodiment, it should be understood that a different number of protector ribs 32 may be incorporated within the present invention. Preferably, the protector ribs 32 are uniformly spaced about the cone protector means 28.

An important aspect of the present invention resides in a plurality of grip rib means 38–40 integrally disposed on an interior surface 42 of the grip portion 20 of the handle protector 10. The plurality of grip rib means 38–40 provide a frictional engagement with the lamp handle 12, as shown in FIG. 3. The plurality of grip rib means 38–40 creates a plurality of spaces 46 to 48, allowing air to enter into the interior of the grip portion 20, thus eliminating any suction force which was encountered with prior art handle covers. Accordingly, the handle cover 10 may be readily removed from the lamp handle 12 upon completion of the surgical procedure. It should be appreciated that the plurality of grip rib means may take various forms, either singularly or in combination with the configuration of the grip portion 20 to accommodate for variations in the diameter of the lamp handle 12 while still providing the proper frictional engagement.

Figure 5:
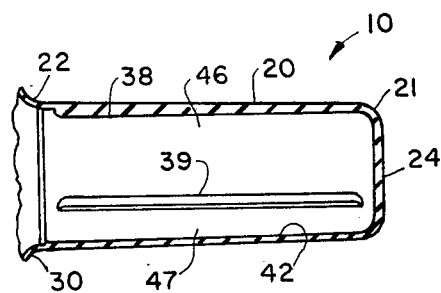
FIG. 5 is an enlarged partial sectional view showing in greater detail the taper of the grip portion and one of the plurality of rib means.

FIG. 5 is an enlarged partial sectional view showing in greater detail the grip rib means and the configuration of the grip portion 20. In this embodiment, the grip portion 20 is tapered along the length thereof, with the first end 21 having a smaller diameter than the second end 22. Additionally, the plurality of rib means are uniformly disposed about the interior surface 42 of the grip portion 20 and extend longitudinally along the length thereof. Each of the grip rib means 38–40 is similarly tapered, having a greater thickness proximate the second end 22 of the grip portion 20 than the thickness proximate the first end 21 of the grip portion 20. Accordingly, the taper of the grip portion 20 complements the taper of the plurality of grip ribs 38–40 to provide the proper frictional engagement, as well as accommodating for variations in the diameter of the handle 12 of the surgical lamp. Of course, the specific dimensions of the handle cover 10 may be altered to accommodate different diameters of lamp handles, but the tapered grip portion and grip rib means accommodates for nominal variations encountered with typical lamp handles of surgical lamps.

Figure 6:
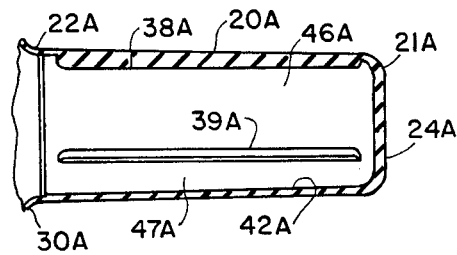
FIG. 6 is an alternate embodiment of the taper of the grip portion and the rib means shown in FIG. 5.

FIG. 6 is a variation of the invention 10 shown in FIGS. 1–5 with similar parts being labelled with a similar number followed by the letter "A". In this embodiment, the grip portion 20A tapers from the second end 22A to the first end 21A in a manner similar to the embodiment shown in FIGS. 1–5. Each of the plurality of grip ribs 38A to 40A extends substantially along the longitudinal length of the grip portion 20A, but are substantially uniform in thickness or cross-sectional area. This embodiment has the advantage wherein the uniform thickness grip ribs 38A to 40A add mechanical strength of the grip portion 20A uniformly along the longitudinal length thereof.

Figure 7:
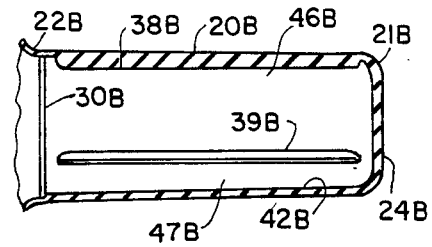
FIG. 7 is another embodiment of the taper of the grip portion and ribs means.
Figure 8:
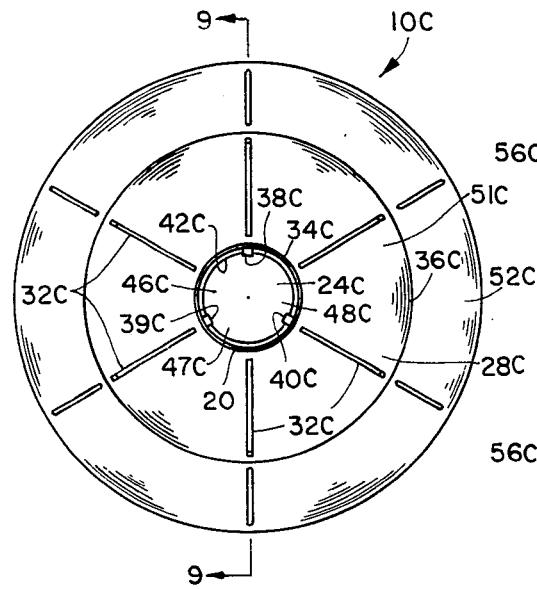
FIG. 8 is a top view of a second embodiment of the present invention.
Figure 9:
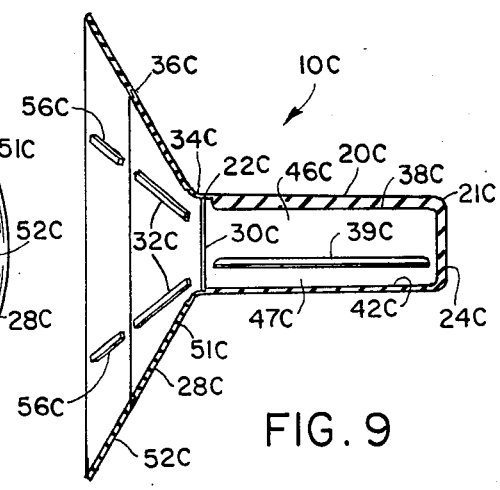
FIG. 9 is a sectional view along 9—9 of FIG. 8.

FIG. 7 is still a further embodiment of the invention 10B shown in FIGS. 1–5, with similar parts being labelled with a similar number followed by the letter "B". In this embodiment, the grip portion 20B is substantially cylindrical between the first and second ends 21B and 22B. Each of the plurality of grip ribs 38B to 40B is tapered along the longitudinal length thereof, with the thickness or cross-sectional area of the grip ribs proximate the second end 22B being less than the thickness or cross-sectional area of the grip rib proximate the first end 21B. This embodiment utilizes a generally cylindrical outer grip portion 20B which may be desirable in some applications.

FIGS. 8–11 show still another embodiment of the present invention 10C, with similar parts being labelled with a similar reference numeral, followed by a letter "C". In this embodiment, the rib means 38C–40C and the grip portion 20C is shown substantially similar to the rib means 38–40 and grip portion 20 shown in FIGS. 1–5. However, it should be appreciated that the grip portion and the rib means may incorporate any of the embodiments heretofore described.

This embodiment provides additional protection for reducing the possibility of contact of the hand 16 with a non-sterile surface. The protector means 28C comprises a first protector 51C connected by first connecting means 30C to the grip portion 20C in a manner similar to FIGS. 1–5. In addition, this embodiment includes a second protector 52C which is integrally connected to the distal edge 36C of the first protector 51C by an integral reduced-wall second connecting means 54C. The second protector 52C also includes protector ribs 56C for adding mechanical strength to the second protector 52. The physical configuration of the first and second protectors 51C and 52C, in conjunction with the second connector means 54C enables the second protector 52C to be in one of two bistable positions.

Figure 10:
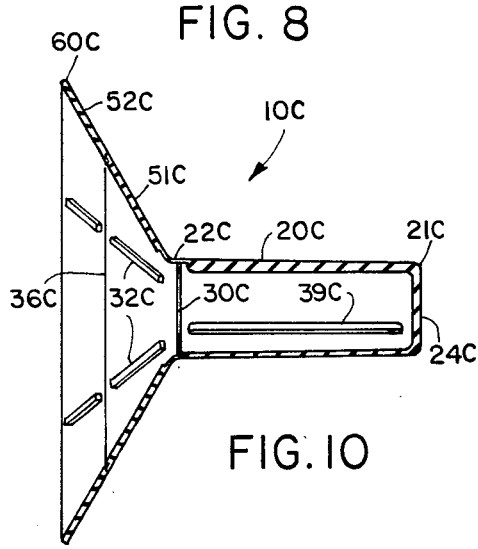
FIG. 10 is a side sectional view of the device of FIGS. 8 and 9 in a first bistable position.

FIG. 10 illustrates a first bistable position wherein the second protector 52C extends in a direction substantially the same as the direction of the first protector 51C. In this position, the second protector 52C offers an additional surface area of protection to the hand 16 of the operator 18.

Figure 11:
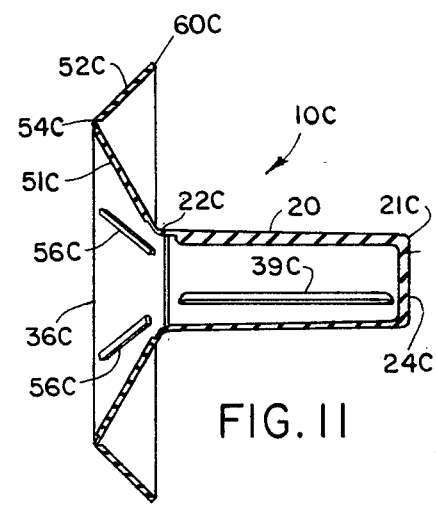
FIG. 11 is a side sectional view of the device of FIGS. 8 and 9 in a second bistable position.

FIG. 11 illustrates a second bistable position wherein the second protector 52C extends at an obtuse angle relative to the first protector 51C. In this position, the distal edge 60C of the second protector 52C functions as a warning or guard to the hand 16 of the operator 18 for locating the grip portion 20C. It is not uncommon for some physicians intent on a critical surgical procedure to reach up for the handle 12 of the surgical lamp 14 without looking toward the handle. In such a procedure, if the hand of the operator is mispositioned, there is a possiblity that the hand may contact a non-sterile surface at the critical surgical procedure. The second bistable position provides a warning or locating surface 60A to the hand 16 of the operator 18 to enable the operator 18 to locate the proper position of the grip portion 20C without contacting a non-sterile surface.

The devices heretofore described may be simply and readily manufactured of a unitary piece of plastic or rubber material and may be conveniently packages in a sterile environment. Preferably, the material has a resiliency for return to an original form, thus enabling the protector means 28 to be flattened in a sterile package and subsequently returned to the originally configuration as shown in the drawings upon removal from a sterile container.

It has been found that a material sold under the trademark "C-Flex" and as disclosed in U.S. Pat. No. 4,386,179 provides a suitable material for the present invention, although other materials may also be suited for use with the present invention.

The present disclosure includes that contained in the appended claims as well as that of the foregoing description. Although this invention has been described in its preferred from with a certain degree of particularity, it is understood that the present disclosure of the preferred form has been made only by way of example and that numerous changes in the details of construction and the combination and arrangement of parts may be resorted to without departing from the spirit and scope of the invention.

What is claim is:

1. A handle protector for covering a lamp handle of a surgical lamp to provide a sterile surface for an operator, comprising:
    a grip portion having a first and a second end;
    an end wall integrally attached to said first end of said grip portion to form a hollow container open at said second end;
    protector means connected to said second end of said grip portion and extending radially outwardly for protecting the hand of the operator from contacting portions of the lamp proximate the lamp handle;
    said protector means including a first and a second protector;
    said first protector having a proximal end and a distal end with said proximal end being connected to said grip portion by a first reduced integral wall thickness;
    said second protector being connected to said distal end of said first protector;
    said second protector being connected to said distal end of said first protector by a second integral reduced wall thickness connector means; and
    a plurality of rib means disposed longitudinally in said grip portion by a first reduced integral wall thickness for frictionally engaging the lamp handle of the lamp.

2. A handle protector as set forth in claim 1, wherein said second connector means enables said second protector to be movable between a first and a second bistable position.

3. A handle protector as set forth in claim 1, wherein said second integral reduced wall thickness connector means enables said second protector to be disposed in one of two bistable positions;
    said first bistable position enabling said second protector to extend in a direction along the direction of said first protector; and
    said second bistable position enabling said second protector to extend at an angle relative to said first protector.

4. A handle protector for covering a lamp handle of a surgical lamp to provide a sterile surface for an operator, comprising:
    a grip portion having a first and a second end;
    an end wall unitarily attached to said first end of said grip portion to form a hollow container open at said second end;
    protector means unitarily connected to said second end of said grip portion and extending radially outwardly for protecting the hand of the operator from contacting portions of the lamp proximate the lamp handle;
    said protector means including a first and a second protector;
    said first protector having a proximal end and a distal end with said proximal end being connected to said grip portion by a first integral wall thickness.
    said second protector being connected to said distal end of said first protector;
    said second protector being connected to said distal end of said first protector by a second integral reduced wall thickness connector means; and
    a plurality of rib means integrally molded to an interior surface of said grip portion and disposed longitudinally in said grip portion for frictionally engaging the lamp handle of the lamp.

5. A handle protector as set forth in claim 4, wherein said second connector means enables said second protector to be movable between a first and a second bistable position.

6. A handle protector as set forth in claim 4, wherein said second integral reduced wall thickness connector means enables said second protector to be disposed in one of two bistable positions;
    said first bistable position enabling said second protector to extend in a direction along the direction of said first protector; and
    said second bistable position enabling said second protector to extend at an angle relative to said first protector.

* * * * *